US008672877B2

(12) United States Patent
Gust

(10) Patent No.: US 8,672,877 B2
(45) Date of Patent: Mar. 18, 2014

(54) NURSING SYSTEMS

(76) Inventor: William David Gust, Wayzata, MN (US)

( * ) Notice: Subject to any disclaimer, the term of this patent is extended or adjusted under 35 U.S.C. 154(b) by 710 days.

(21) Appl. No.: 12/943,610

(22) Filed: Nov. 10, 2010

(65) Prior Publication Data

US 2011/0108504 A1 May 12, 2011

Related U.S. Application Data

(60) Provisional application No. 61/260,534, filed on Nov. 12, 2009.

(51) Int. Cl.
*A61M 1/06* (2006.01)

(52) U.S. Cl.
USPC ............................... 604/76; 119/71; 215/11.4

(58) Field of Classification Search
CPC ........................................................ A61M 1/06
USPC ................... 119/71, 72.5; 215/11.4; 220/705; 248/102, 104, 106, 107; 604/74, 76
See application file for complete search history.

(56) References Cited

U.S. PATENT DOCUMENTS

| | | | | |
|---|---|---|---|---|
| 2,760,664 | A * | 8/1956 | Amico et al. | 215/11.1 |
| 3,757,784 | A * | 9/1973 | Avery | 604/76 |
| 4,301,934 | A * | 11/1981 | Forestal | 215/11.4 |
| 4,669,461 | A * | 6/1987 | Battaglia et al. | 128/202.15 |
| 4,687,466 | A * | 8/1987 | Larsson | 604/82 |
| 5,474,193 | A * | 12/1995 | Larsson et al. | 215/11.4 |
| 8,141,728 | B1 * | 3/2012 | Dahler et al. | 215/11.4 |
| 2004/0188372 | A1 * | 9/2004 | Ruth et al. | 215/11.4 |
| 2008/0045888 | A1 * | 2/2008 | Edwards et al. | 604/76 |
| 2010/0292637 | A1 * | 11/2010 | Sokal et al. | 604/76 |

OTHER PUBLICATIONS

Medela, Inc., The SNS™, Supplemental Nursing System for Breastfeeding Assistance, © 2001, 54 pages.

* cited by examiner

*Primary Examiner* — Nicholas Lucchesi
*Assistant Examiner* — Gerald Landry, II
(74) *Attorney, Agent, or Firm* — Merchant & Gould P.C.

(57) ABSTRACT

A nursing system includes a fluid delivery module mounted to a portion of a human body. The fluid delivery module is coupled to a fluid source via a channel. A feeding recipient latches-on to a portion of the delivery module to draw fluid from the fluid source, thereby simulating conventional breast-feeding.

17 Claims, 3 Drawing Sheets

NURSING SYSTEMS

BACKGROUND

In many instances, feeding an infant or young child with milk directly from the breast can be problematic. For example, issues such as premature delivery, insufficient or delayed lactation, mastitis, and others may complicate or preclude conventional breastfeeding. For these and other reasons, an alternative to nursing directly from the breast may be desired.

SUMMARY

In one example aspect, a nursing system is disclosed. The nursing system includes: a fluid source including an inlet and an outlet; a fluid module including a cavity configured to receive a portion of a terminal member of a hand; and a fluid channel including a first end and a second end. The first end is coupled to the outlet of the fluid source and the second end is coupled to the fluid module forming a continuous fluid flow path therebetween, and fluid is drawn from the fluid source through the fluid channel to the fluid module upon application of at least one external force.

In another example aspect, a nursing assembly is disclosed. The nursing assembly includes: a source including an inlet and an outlet; a dispenser including a cavity configured to receive a portion of a breast; and a channel including a first end and a second end. The first end is coupled to the outlet of the source and the second end is coupled to the dispenser forming a continuous fluid flow path therebetween, and fluid is drawn from the source through the channel to the dispenser upon application of at least one external force.

In yet another example aspect, an apparatus for nursing an infant is disclosed. The apparatus includes a fluid source module including a reservoir in fluid connection with a source outlet; a fluid delivery module formed of a pliable material including a recipient outlet adjacent and in fluid connection with a cavity configured to receive one of: a portion of a terminal member of a human hand; and a human breast; and a fluid channel comprising a medical grade tubing and including a first end and a second end. The first end is coupled to the source outlet and the second end is coupled to the recipient outlet forming a continuous fluid flow path therebetween, and fluid is drawn from the fluid source through the fluid channel to the fluid module upon application of at least one external force.

DESCRIPTION OF THE DRAWINGS

Aspects of the disclosure may be more completely understood in consideration of the following detailed description of various embodiments of the disclosure in connection with the accompanying drawings.

DETAILED DESCRIPTION

The example embodiments described in the following disclosure are provided by way of illustration only and should not be construed as limiting. Various modifications and changes may be made to the example embodiments described below without departing from the true spirit and scope of the disclosure.

The present disclosure generally relates to nursing an infant or young child. More specifically, the present disclosure relates to a nursing assembly that simulates nursing with milk directly from the breast.

In example embodiments provided herein, a nursing system includes a fluid delivery module generally mounted to a portion of a human body. The fluid delivery module is coupled to a fluid source via a channel. A feeding recipient latches-on to a portion of the delivery module to draw fluid from the fluid source, thereby simulating conventional breastfeeding (i.e., nursing with milk directly from the breast). Although the present disclosure is not so limited, an appreciation of the various aspects of the disclosure will be gained through a discussion of the examples provided below.

Figure 1:
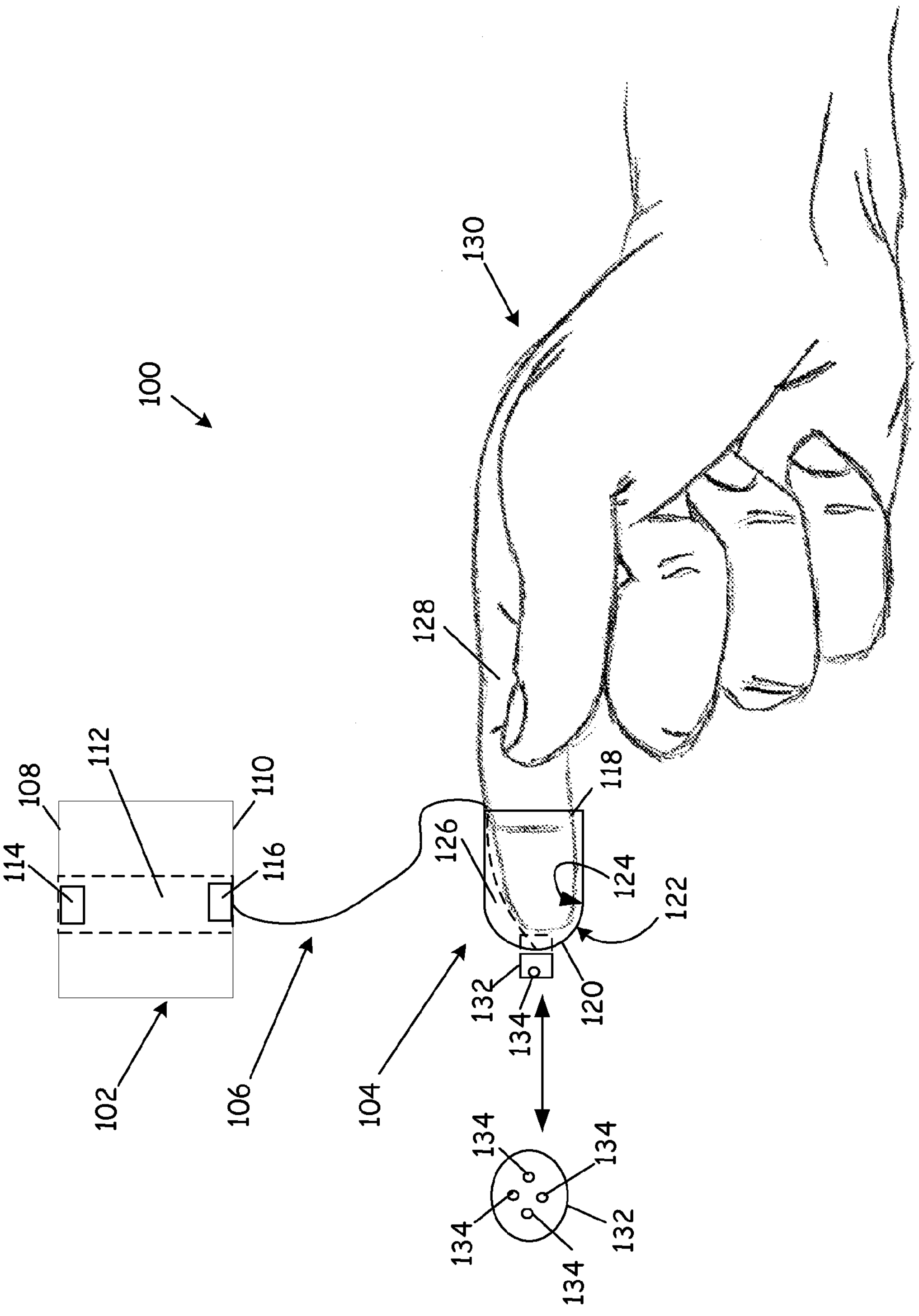
FIG. 1 is a schematic view of a first example nursing system.

Referring now to FIG. 1, a schematic view of a first example nursing assembly 100 is shown. In general, the nursing assembly 100 includes a fluid source 102, a fluid delivery module 104, and a channel 106 coupled together in a series connection.

The example fluid source 102 is generally a rigid or flexible container and includes a first end 108 and a second end 110 connected by a reservoir 112 internal to the fluid source 102. Adjacent to the first end 108 is an inlet 114 by which a fluid (e.g., breast milk, formula) is introduced and stored within the reservoir 112. Similarly, adjacent to the second end 110 is an outlet 116 by which fluid is evacuated from the reservoir 112 via at least one externally applied force (e.g., suction, gravity), as described further below. Other embodiments of the fluid source 102 are possible as well.

The example fluid delivery module 104 is generally thimble-shaped and formed from a soft, pliable material which may be one of transparent (as depicted in FIG. 1), partially transparent, and opaque. In some examples, the fluid delivery module 104 is made of a material such as a silicone or other thermoplastic elastomer.

The fluid delivery module 104 includes a first end 118, a second end 120, an external surface 122, and an internal surface 124. In general, the external surface 122 tapers with slight curvature in a direction extending from the first end 118 to the second end 120. However, other embodiments are possible. For example, the external surface 122 may exhibit a more or less pronounced taper extending in a direction from the first end 118 to the second end 120 to assume the shape of, for example, a bulbous knob or a nipple. Still other embodiments are possible as well.

The fluid delivery module 104 additionally forms a cavity 126. The cavity 126 is configured to receive a portion of a finger 128 of a human hand 130. In the example shown, the finger 128 is a forefinger. However, any terminal member of the hand 130 may be positioned within the cavity 126. Additionally, any it will be appreciated that any other rigid or semi-rigid support structure may be positioned within the cavity 126 to support the fluid delivery module 104.

The fluid delivery module 104 further includes a recipient outlet 132 adjacent to the second end 120. In certain embodiments, the recipient outlet 132 is a one-way valve. However, other embodiments are possible as well. In the example shown, the recipient outlet 132 extends outwardly from the second end 120 and includes a portion positioned internal to the fluid delivery module 104. However, other embodiments are possible. For example, the recipient outlet 132 may extend to a flush position with respect to the second end 120. In other examples, the recipient outlet 132 can simply be an aperture or other structure that is used to deliver milk or formula, as described below. Still other embodiments are possible.

The recipient outlet 132 includes one or more fluid dispensing apertures 134 of a predetermined geometry and geometric configuration. In one example, the recipient outlet 132 includes a single rectangular aperture. In other embodiments, the recipient outlet 132 may include a plurality of circular apertures 134 arranged in a circular configuration. Other geometries and geometric configurations of the one or more fluid dispensing apertures 134 are possible.

In the example shown, the channel 106 is positioned within the fluid delivery module 104 through the first end 118, with a portion of the channel 106 internal to the fluid delivery module 104. In the example embodiment, the portion of the channel 106 internal to the fluid delivery module 104 is positioned adjacent to the internal surface 124 of the fluid delivery module 104 and thus accessible within cavity 126. However, other embodiments are possible as well.

As mentioned above, the fluid source 102, fluid delivery module 104, and channel 106 are coupled together in a series connection. Specifically, the channel 106 is tubing (e.g., medical grade tubing) connected between the outlet 116 of the fluid source 102 and the recipient outlet 132 of the fluid delivery module 104. In this manner, a continuous fluid flow path is formed between the fluid source 102 and the fluid delivery module 104. In use, a recipient (e.g., a mammal, such as a human baby) latches-on to the external surface 122 of the fluid delivery module 104 and upon application of suction draws fluid from the fluid source 102. It will appreciated that gravity may assist evacuation of fluid from the fluid source 102.

Figure 2:
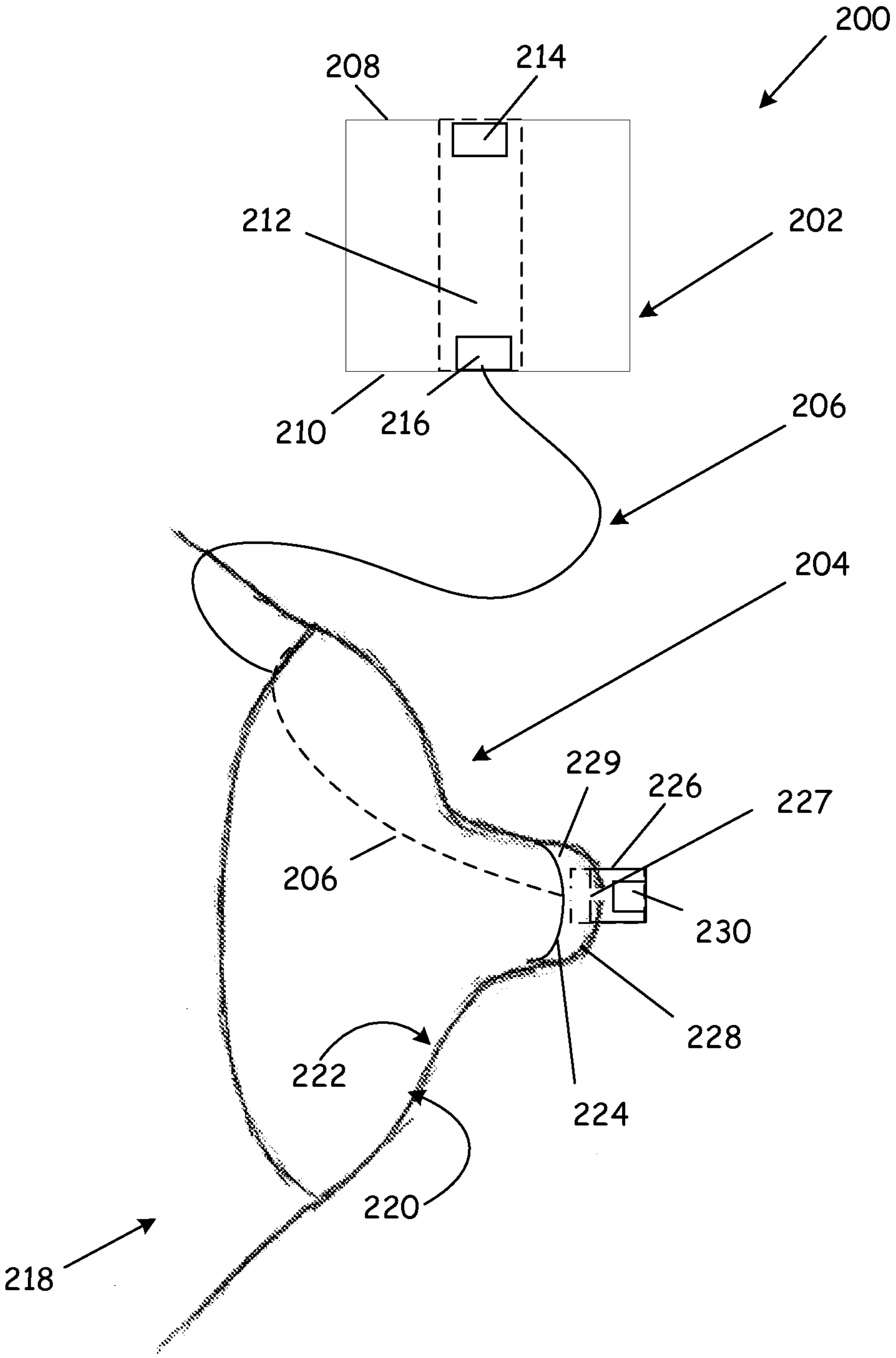
FIG. 2 is a schematic view of a second example nursing system.

Referring now to FIG. 2, a schematic view of another example nursing assembly 200 is shown. The nursing assembly 200 includes a fluid source 202, a fluid delivery module 204, and a channel 206 coupled together in a series connection.

In general, the example fluid source 202 is configured substantially similar to the fluid source 102 described above with respect to FIG. 1. For example, the example fluid source 202 is generally a rigid or flexible container and includes a first end 208 and a second end 210 connected by a reservoir 212 internal to the fluid source 202. Adjacent to the first end 208 is an inlet 214 by which a fluid is introduced and stored within the reservoir 212. Similarly, adjacent to the second end 210 is an outlet 216 by which fluid is evacuated from the reservoir 212 via at least one externally applied force. Other embodiments of the fluid source 202 are possible as well.

The example fluid delivery module 204 is generally nipple-shaped and is formed from a soft, pliable material which may be one of transparent (as depicted in FIG. 2), partially transparent, and opaque.

In the example shown, the fluid delivery module 204 is positioned on a breast 218, in a manner similar to that of a nipple shield. The fluid delivery module 204 includes an external surface 220, an internal surface 222, and a nipple 224. The fluid delivery module 204 further includes a recipient outlet 226 adjacent to an end portion 228 of the fluid delivery module 204. In certain embodiments, the recipient outlet 226 is a one-way valve. However, other embodiments are possible.

The recipient outlet 226 extends outwardly from the end portion 228, with a portion positioned internal to the fluid delivery module 204. Other embodiments are possible. For example, the recipient outlet 226 may extend to a flush position with respect to the end portion 228. In other examples, the recipient outlet 226 can be eliminated, and an aperture can be formed in the fluid delivery module 204. Still other embodiments are possible as well.

The recipient outlet 226 includes one or more fluid dispensing apertures 230 of a predetermined geometry and geometric configuration. In the example shown, the recipient outlet 226 includes a single rectangular aperture. In other embodiments, the recipient outlet 226 may include a plurality of circular apertures arranged in a circular configuration. In general, any geometry and/or geometric configuration of the one or more fluid dispensing apertures 230 are possible.

As mentioned above, the fluid source 202, fluid delivery module 204, and channel 206 are coupled together in a series connection. Specifically, the channel 206 is tubing (e.g., medical grade tubing, etc.) connected between the outlet 216 of the fluid source 202 and the recipient outlet 226 of the fluid delivery module 204. In this manner, a continuous fluid flow path is formed between the fluid source 202 and fluid delivery module 204. In the example shown, a portion of the channel 206 is positioned between the breast 218 and the internal surface 222 of the fluid delivery module 204.

In use, a recipient latches-on to the external surface 220 of the fluid delivery module 204, and, upon application of suction (and/or assisted by gravity), fluid is drawn from the fluid source 202.

In some examples, the fluid delivery module 204 includes one or more apertures 227 formed at the location of the nipple. The aperture 227 can allow colostrum produced by the breast to move through the apertures 227, mix with the formula from by the fluid delivery module 204, and be delivered to the recipient.

In yet another example, the recipient outlet 226 need not be included. Instead, the channel 206 can be positioned to terminate in the space 229 between the nipple 224 and the end portion 228 of the fluid delivery module 104. The fluid can then be delivered through the apertures 227.

Figure 3:
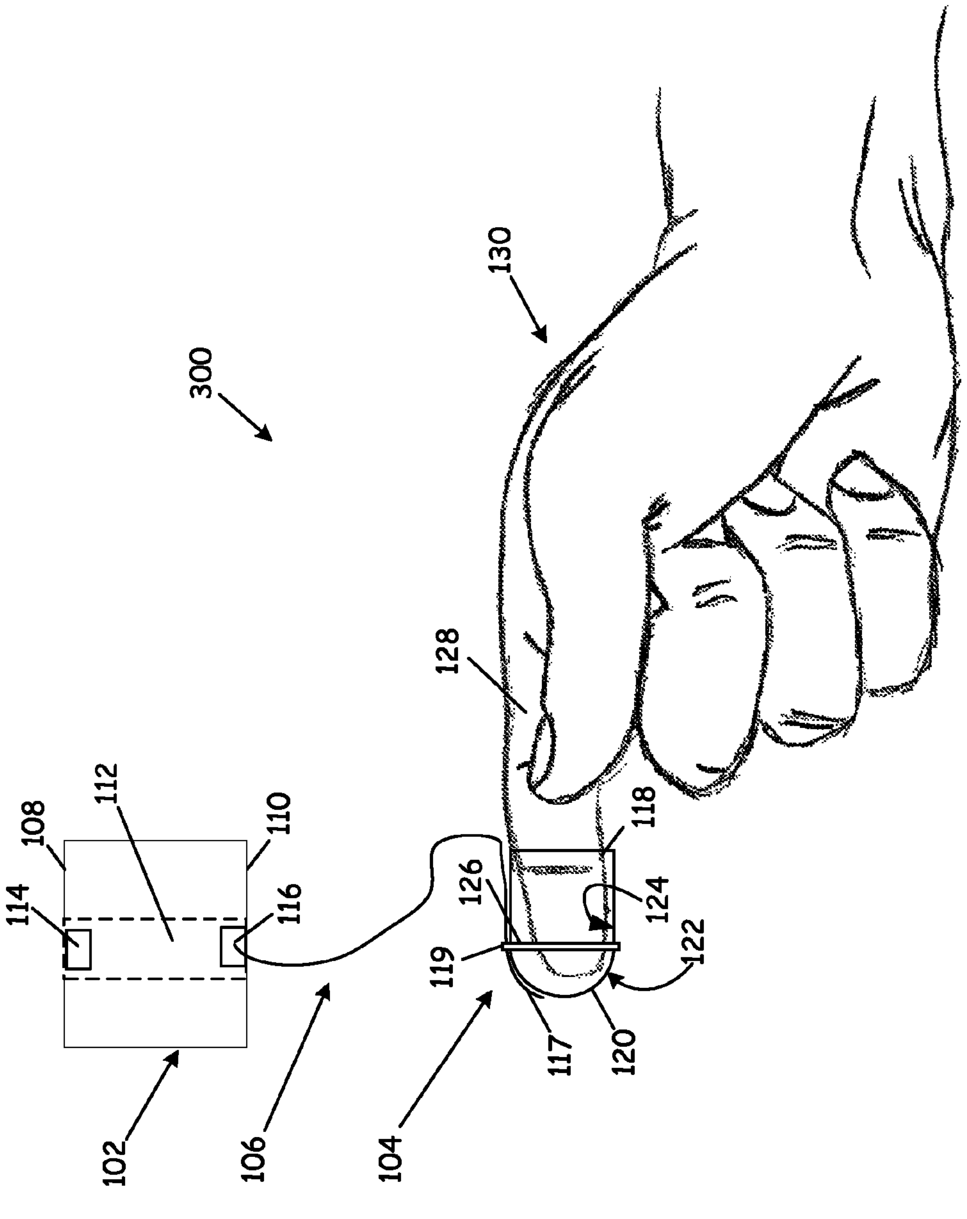
FIG. 3 is a schematic view of a third example nursing system.

Alternative designs are possible. For example, referring now to FIG. 3, another schematic view of a third example nursing assembly 300 is shown. The nursing assembly 300 is similar to that of the nursing assembly 100 described above, except that nursing assembly 300 includes an elastic ring or band 119 positioned about the fluid delivery module 104. The band 119 holds the channel 106 in place on the external surface 122, rather than running the channel 106 underneath the fluid delivery module 104 adjacent the internal surface 124. In this configuration, the band 119 holds the channel 106 so that an end 117 of the channel 106 is positioned at a desired location for delivery of the fluid.

Multiple bands can be provided to further retain the channel 106 as needed. In some examples, the bands can be formed separately from the fluid delivery module 104. In other examples, the bands can be formed integrally with the fluid delivery module 104. A similar band could be used with the nursing assembly 200 shown in FIG. 2 as well. Other configurations are possible.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A nursing system, comprising:

a fluid source including an inlet and an outlet;

a fluid module including a cavity configured to receive a portion of a terminal member of a hand;

a fluid channel including a first end and a second end, wherein the first end is coupled to the outlet of the fluid source and the second end is coupled to the fluid module forming a continuous fluid flow path therebetween; and at least one securing member positioned relative to the fluid module to secure the channel to an outer surface of the fluid module, wherein the at least one securing member is formed as an elastic ring, wherein fluid is drawn from the fluid source through the fluid channel to the fluid module upon application of at least one external force.

2. The nursing system of claim 1, wherein the fluid module further includes an outlet comprising one or more fluid dispensing apertures, and wherein the second end of the channel is connected to the outlet.

3. The nursing system of claim 2, wherein the outlet includes a one-way valve.

4. The nursing system of claim 1, further comprising at least one securing member positioned to the fluid module to secure the channel to an outer surface of the fluid module.

5. The nursing system of claim 4, wherein the at least one securing member is one of: formed separately from the fluid module; and formed integrally with the fluid module.

6. The nursing system of claim 1, wherein the fluid module is shaped as one of: thimble-shaped; and nipple-shaped.

7. The nursing system of claim 6, wherein the fluid module is formed of a pliable material.

8. The nursing system of claim 7, wherein pliable material is one of: transparent; partially transparent; and opaque.

9. The nursing system of claim 1, wherein the channel includes medical grade tubing.

10. A nursing assembly, comprising:

a source including an inlet and an outlet;

a dispenser including a cavity configured to receive a portion of a breast; and a channel including a first end and a second end, wherein the first end is coupled to the outlet of the source and the second end is coupled to the dispenser forming a continuous fluid flow path therebetween;

wherein fluid is drawn from the source through the channel to the dispenser upon application of at least one external force; and wherein the dispenser further includes an outlet comprising one or more fluid dispensing apertures, and wherein the second end of the channel is connected to the outlet.

11. The nursing assembly of claim 10, wherein the outlet is a one-way valve.

12. The nursing assembly of claim 10, wherein the dispenser further includes one or more apertures formed at a location of a nipple of the breast when the dispenser is positioned thereto for mixing of colostrum with the fluid of the source.

13. The nursing assembly of claim 10, further comprising at least one elastic securing member positioned to the dispenser to secure the channel to an outer surface of the dispenser.

14. The nursing assembly of claim 13, wherein the at least one elastic securing member is one of: formed separately from the dispenser; and integrally formed with the dispenser.

15. A nursing assembly, comprising:

a source including an inlet and an outlet a dispenser including a cavity configured to receive a portion of a breast and a channel including a first end and a second end, wherein the first end is coupled to the outlet of the source and the second end is coupled to the dispenser forming a continuous fluid flow path therebetween;

wherein fluid is drawn from the source through the channel to the dispenser upon application of at least one external force; and wherein the dispenser is formed from a pliable material and shaped as one of: thimble-shaped; and nipple-shaped.

16. The nursing assembly of claim 15, wherein the pliable material is one of: transparent; partially transparent; and opaque.

17. The nursing assembly of claim 10, wherein the channel is a medical grade tubing.

* * * * *